United States Patent
Yang (10) Patent No.: US 10,219,714 B2
(45) Date of Patent: Mar. 5, 2019

(54) ELECTRIC CONDUCTIVE SENSING DEVICE

(71) Applicant: Wandy Rubber Industrial Co., Ltd., New Taipei (TW)

(72) Inventor: Janis Yang, New Taipei (TW)

(73) Assignee: Wandy Rubber Industrial Co., Ltd., New Taipei (TW)

( * ) Notice: Subject to any disclaimer, the term of this patent is extended or adjusted under 35 U.S.C. 154(b) by 345 days.

(21) Appl. No.: 15/181,639

(22) Filed: Jun. 14, 2016

(65) Prior Publication Data

US 2017/0231520 A1 Aug. 17, 2017

(30) Foreign Application Priority Data

Feb. 17, 2016 (TW) .............................. 105202294 U (51) Int. Cl.
*A61B 5/0408* (2006.01)
*A61B 5/0416* (2006.01)

(52) U.S. Cl.
CPC ........ *A61B 5/04085* (2013.01); *A61B 5/0416* (2013.01); *A61B 5/04087* (2013.01); *A61B 2562/0209* (2013.01); *A61B 2562/164* (2013.01); *A61B 2562/166* (2013.01); *A61B 2562/227* (2013.01)

(58) Field of Classification Search
CPC ................................................ A61B 5/04085
USPC ......................................................... 600/393
See application file for complete search history.

(56) References Cited

U.S. PATENT DOCUMENTS

| | | | | |
|---|---|---|---|---|
| 4,353,372 A | * | 10/1982 | Ayer ................. | A61B 5/04085 174/117 FF |
| 4,763,660 A | * | 8/1988 | Kroll ................. | A61B 5/04085 439/77 |
| 5,511,553 A | * | 4/1996 | Segalowitz ......... | A61B 5/0006 128/903 |
| 5,868,671 A | * | 2/1999 | Mahoney ........... | A61B 5/04085 600/382 |
| 6,076,003 A | * | 6/2000 | Rogel ................ | A61B 5/04085 600/390 |
| 6,453,186 B1 | * | 9/2002 | Lovejoy ............. | A61B 5/04085 600/386 |

(Continued)

*Primary Examiner* — Lee S Cohen
(74) *Attorney, Agent, or Firm* — Alan D. Kamrath; Kamrath IP Lawfirm, P.A.

(57) ABSTRACT

An electric conductive sensing device includes a front sheet of a sensing pad having several openings. A sensing electrode is a conductive ink electrode aligned with and exposed through each opening. Several first terminals are formed on an insert portion of the sensing pad and are connected to sensing electrodes. Each opening covered by a conductive gel is electrically connected to the corresponding sensing electrode. The insert portion is integrated in a connector. The electric conductive sensing device can be used as electrode patches of ECG devices or electric stimulators. In use, the connector is plugged into the devices to transmit tiny electrical currents to the ECG device from the human skin surface, or to transmit electrical currents generated from the stimulator to the human. The sensing electrodes are formed by conductive ink printing thereby simplifying the manufacturing process and lowering the manufacturing cost compared to conventional soldered structures.

8 Claims, 9 Drawing Sheets

(56) References Cited

U.S. PATENT DOCUMENTS

| | | | | |
|---|---|---|---|---|
| 6,751,493 B2* | 6/2004 | Wenger | ............. | A61B 5/04085 |
| | | | | 600/382 |
| 9,510,762 B2* | 12/2016 | Datovech | ........... | A61B 5/04085 |
| 2002/0133069 A1* | 9/2002 | Roberts | ............. | A61B 5/04085 |
| | | | | 600/382 |
| 2003/0068914 A1* | 4/2003 | Merry | ............... | A61B 5/04286 |
| | | | | 439/259 |

* cited by examiner

ELECTRIC CONDUCTIVE SENSING DEVICE

FIELD OF THE INVENTION

The present invention relates to an electric current conductive pad and, more particularly, to an electric conductive sensing device capable of detecting electric current or conducting electric stimulations.

BACKGROUND OF THE INVENTION

An electrocardiogram (ECG) is a diagnostic technique that periodically monitors and records heart electrophysiological activities by electrodes placed on the skin surface. The principle of ECG is that, while tiny electrical signals are generated on the skin surface that arise from the depolarization and repolarization of myocardial cells during each heartbeat, those electrical signals will be captured and amplified by ECG recording or monitoring devices to produce the ECG diagrams of the person being tested.

The structure used for capturing changes of electrical signals on the skin surface can be an ECG patch. The surface of such ECG patch has several button-like electrodes. While in use, conductive gels will be spread on the surface of the electrodes, and the electrodes will be adhered to the skin surface on the chest of the person to be tested for capturing electrical signals generated from heartbeats. These signals will eventually be transmitted to ECG devices to produce the ECG diagrams.

Although conventional ECG patches are fully capable of precisely detecting tiny electrical signals on the human skin surface, the button-like electrodes on the ECG patch is, however, connected to the electrical circuit on the patch by soldering or buckling, so that the manufacturing process may be more complex because each button-like electrode needs to be soldered or buckled to combine with the patch. Consequently, the manufacturing costs are hard to be effectively reduced, and the overall cost of such kind of product will be high.

Other than the aforementioned ECG patch, the electrode patches used for electric stimulation such as transcutaneous electrical nerve stimulation (TENS) are also capable of transmitting electrical signals. Contrary to the ECG that transmits electric signals from the skin to the device, these kinds of electrode patches transmit electrical signals generated by, for instance, a transcutaneous electrical nerve stimulator to the human body, to create effects such as massage or rehabilitation.

The structure of the aforementioned electrode patch is quite similar to the conventional ECG patch, and they all include multiple button-like electrodes. The button-like electrodes all need to be soldered or buckled for connecting to the electrical circuit of the patch. As mentioned above, these kinds of structure are not easily manufactured due to the complexity of the process, thus causing a shortcoming of high cost.

SUMMARY OF THE INVENTION

As conventional structures for capturing tiny electrical signals from the human skin surface, such as ECG patches, need to be soldered or buckled with button-like electrodes, these processes cause higher manufacturing costs. Therefore, the present invention provides a structure containing printed sensing electrodes, which is also operated with a connector, in order to not only sense tiny electrical signals with reduced manufacturing costs, but also obtain robustness and generate less debris caused by physical frictions while in use.

An aspect of the present invention is to provide an electric conductive sensing electrode, including:

A sensing pad has a front sheet and a rear sheet combined with the front sheet, with the front sheet having at least one opening, an electric film sandwiched between the front sheet and the rear sheet, an insert portion extended from a side of the electric film, a sensing electrode formed on the electric film and aligned with each of the at least one opening, with each of the sensing electrodes being a conductive ink electrode and exposed through each of the openings, and at least one first terminal formed on the insert portion. Each of the first terminal and the corresponding sensing electrode of the first terminal are connected together by a first electric circuit, each of the at least one opening is covered by a conductive gel, and each of the conductive gel electrically connected with each of the sensing electrodes by directly contacting.

A connector has the insert portion of the sensing pad integrated in a tongue plate installed in the connector. At least one first output terminal is disposed on the tongue plate, with each of the at least one first output terminal electrically connected with each of the first terminal.

While practicing the present invention as an ECG patch for example, the front side of the sensing pad is adhered to a human chest. By contacting the human skin through the conductive gel, the tiny electric signals generated on the skin surface during each heartbeat will be transmitted to the first terminal and the corresponding first output terminal on the connector through the sensing electrode. When the connector is further connected to an ECG device, the tiny electric signals detected by the sensing pad will be transmitted to the ECG device. Then, the tiny electric signals will be amplified and transformed into final results, i.e. an ECG diagram.

Benefits of the present invention are as follows.

Because the sensing electrode is a printed electrode formed of conductive ink, no solder process is needed while manufacturing, the overall manufacturing process is more simplified, and the costs are relatively lower than manufacturing conventional electrodes.

The insert portion of the sensing pad transmits the electrical signals received by the sensing pad to a device capable of receiving and processing signals, such as an ECG device, through a connector. Therefore, the insert portion does not need to be directly plugged into an ECG device, and no debris of the insert portion will be left in the plug of the device, which easily causes damages.

The conventional ECG patches are designed to attach on user's chests one by one in proper position. It is troublesome to allocate these ECG patches at proper positions to receive correct electrical signals. On the contrary, the present invention provides integrated multiple sensing electrodes on one sensing pad to reduce the procedure of installing the sensing electrodes on the human's body. The present invention provides a simpler and easier way to place sensing electrodes at proper positions.

BRIEF DESCRIPTION OF THE DRAWINGS

The structure and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

The structure and technical features of the present invention will now be described in considerable detail with reference to some embodiments and the accompanying drawings thereof, so that the present invention can be easily understood.

Figure 1:
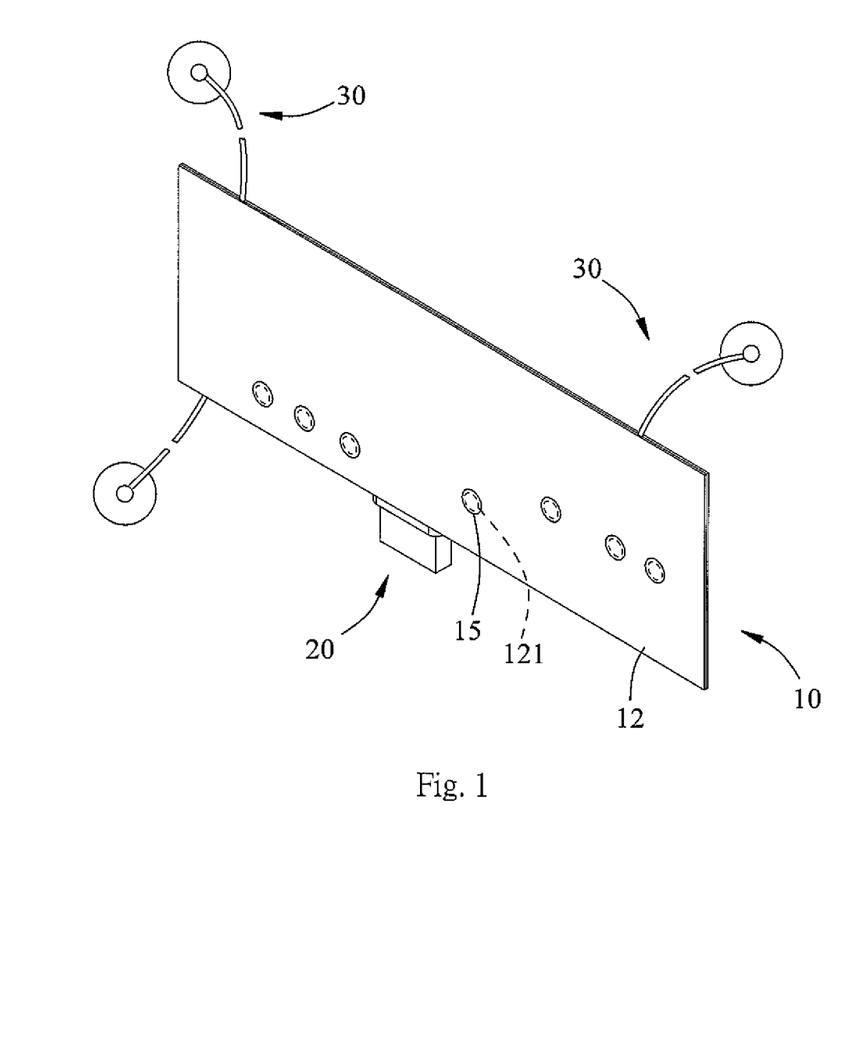
FIG. 1 is a perspective view illustrating a first preferred embodiment of the present invention.

Please refer to FIG. 1 illustrating a first embodiment of the present invention, which provides an electric conductive sensing device including ECG electrode patches. The electric conductive sensing device includes a sensing pad 10, a connector 20 combined with the sensing pad 10, and three extended electrode structures 30 connected to the sensing pad 10. The number of the extended electrode structures 30 is not limited to three.

Figure 2:
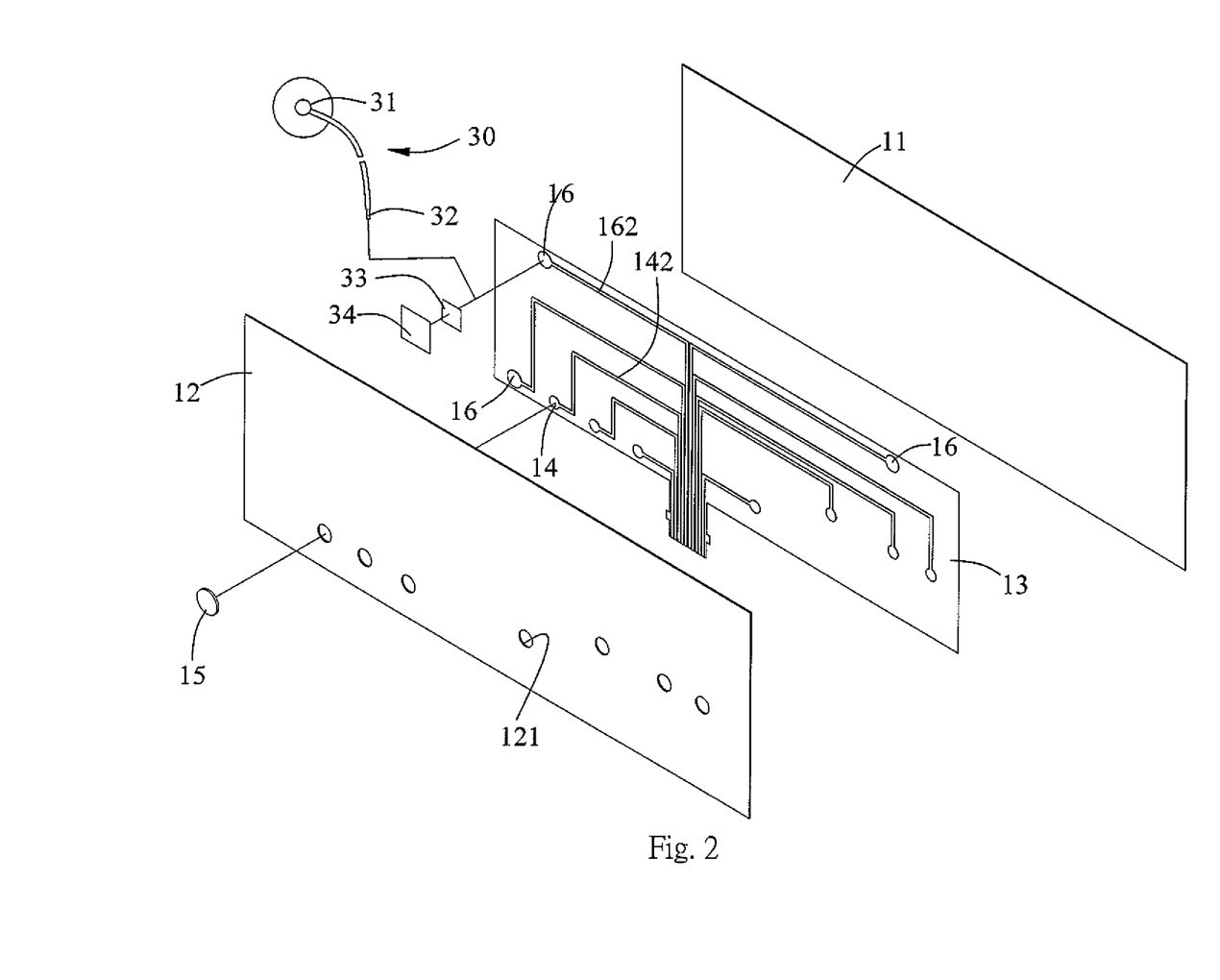
FIG. 2 is an exploded diagram illustrating a sensing pad and an extended electrode structure according to the first embodiment of the present invention.
Figure 3:
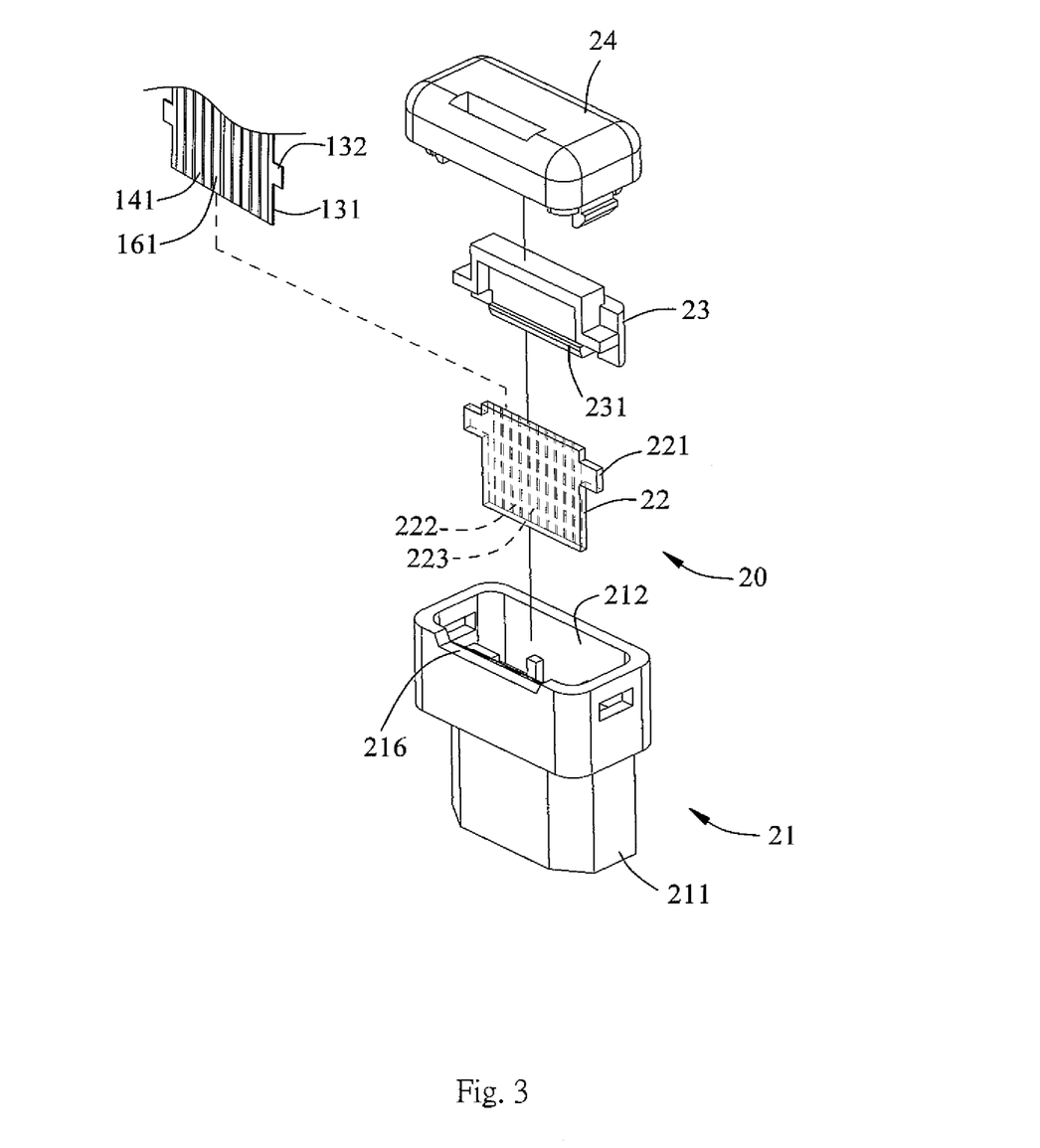
FIG. 3 is an exploded diagram illustrating a connector according to the first embodiment of the present invention.

Referring to FIG. 1 to FIG. 3, the sensing pad 10 has a rear sheet 11. The rear sheet 11 is a flexible horizontal rectangular sheet. The front side of the rear sheet 11 is adhesive. A front sheet 12 is disposed on the front side of the rear sheet 11, and the front sheet 12 is a flexible sheet having the identical shape with the rear sheet 11. The periphery of the backside of the front sheet 12 is adhered with the periphery of the front side of the rear sheet 11, and the front side of the front sheet 12 is adhesive. Seven openings 121 are located along the horizontal extension direction of the front sheet 12. The openings 121 may be circular holes, and an electric film 13 is sandwiched between the front sheet 12 and the rear sheet 11. The electric film 13 is a flexible rectangular plastic film, where the area of the electric film 13 is smaller than the area of the front sheet 12 and the rear sheet 11. An insert portion 131 is extended downwardly from the middle of the bottom side of the electric film 13. The insert portion 131 is a rectangular plastic film, and the insert portion 131 is protruded out of the bottom edges of the rear sheet 11 and the front sheet 12. Two positioning protrusions 132 are respectively protruded from the left side and the right side of the insert portion 131.

Corresponding to each of the seven openings 121, a sensing electrode 14 is formed at the front side of the electric film 13. The sensing electrodes 14 are formed of conductive ink and are printed on the surface of the electric film 13. The sensing electrodes 14 are circular, and each of the sensing electrodes 14 is exposed from the opening 121. Corresponding to the number of the sensing electrodes 14, seven first terminals 141 are formed on the insert portion 131. The seven first terminals 141 are spaced horizontally. Each of the first terminals 141 is formed of conductive ink and is printed on the surface of the insert portion 131. Each of the first terminals 141 is connected to the corresponding sensing electrode 14 by a first electric circuit 142. The first electric circuit 142 is formed of conductive ink and is printed on the surface of the electric film 13. Each of the openings 121 is covered by a conductive gel 15. Each of the conductive gels 15 is contacted with a sensing electrode 14 for electrically connecting with the sensing electrode 14.

Three connecting electrodes 16 are formed at the front side of the electric film 13, where each of the connecting electrodes 16 is a conductive ink electrode printed on the surface of the electric film 13. The connecting electrode 16 is circular shaped, and the area of each connecting electrode 16 is larger than the area of the corresponding sensing electrode 14. Corresponding with the number of the connecting electrodes 16, three second terminals 161, which are spaced horizontally with the seven first terminals 141, are formed on the insert portion 131. Each of the second terminals 161 is a conductive ink terminal printed on the surface of the electric film 13. A second electrical circuit 162 is connected between each of the second terminals 161 and the corresponding connecting electrodes 16. The second electrical circuit 162 is a conductive ink circuit printed on the surface of the electric film 13.

Figure 4:
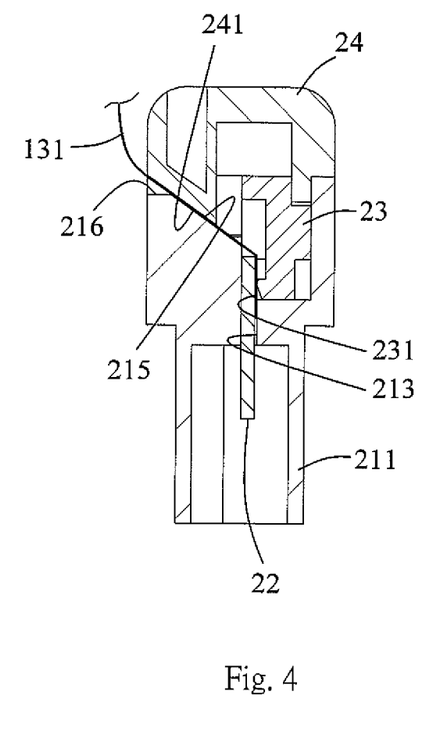
FIG. 4 is a cross-sectional view of the connector according to the first embodiment of the present invention.
Figure 5:
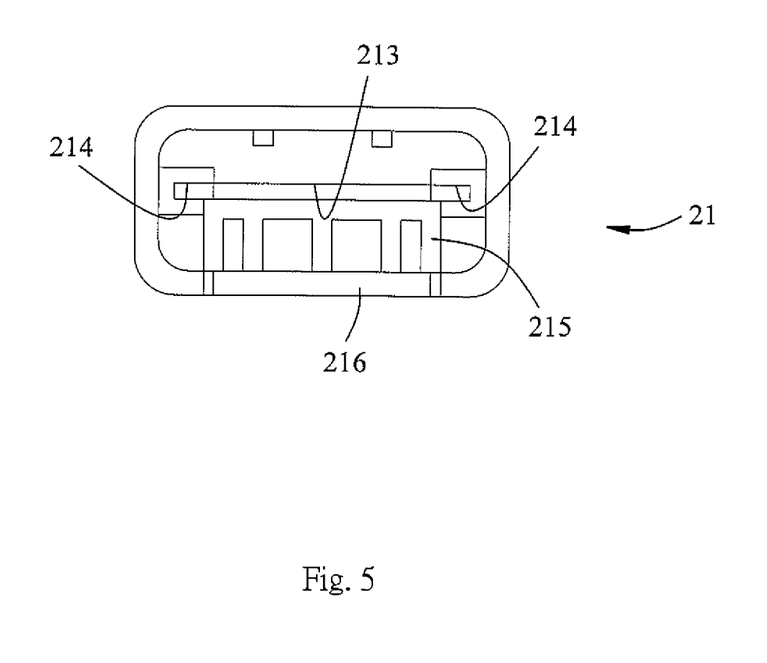
FIG. 5 is a top view of a housing according to the first embodiment of the present invention.

Referring to FIG. 3 to FIG. 5, the connector 20 has a housing 21, the bottom of the housing 21 has a port 211, and the top of the housing 21 has an assembling recess 212. A tongue slot 213 is penetrated throughout the assembling recess 212 and the port 211. Two positioning grooves 214 are respectively located at both sides of the tongue slot 213. A lower inclined plane 215 is interiorly formed at the front side of the assembling recess 212, and the edge of the top of the front side of the housing 21 has a notch 216 joining the lower inclined plane 215.

The electric conductive sensing device also includes a tongue plate 22, where the tongue plate 22 is a rectangular circuit board and is penetrated through the tongue slot 213. The bottom of the tongue plate 22 is inserted into the port 211. The tongue plate 22 has two positioning flanges 221 respectively protruded from the left side and the right side of the tongue plate 22, and the two positioning flanges 221 are respectively received by the two positioning grooves 214 thereby positioning the tongue plate 22 inside the housing 21. The surface of the tongue plate 22 has seven spaced first output terminals 222 horizontally spaced with three second output terminals 223. The insert portion 131 of the sensing pad 10 is inserted into the notch 216, along the lower inclined plane 215, and finally lapping the upper surface of the tongue plate 22. The two positioning protrusions 132 of the insert portion 131 are respectively received by the two positioning grooves 214, thereby positioning the insert portion 131 inside the housing 21, electrically connecting each of the first terminals 141 to the corresponding first output terminal 222, and electrically connecting each of the second terminals 161 to the corresponding second output terminal 223.

A pressing block 23 is located in the assembling recess 212 of the housing 21 and has a pressing portion 231 horizontally protruded toward a side of a surface of the tongue plate 22. The pressing portion 231 presses against the insert portion 131, thereby tightly pressing the insert portion 131 of the sensing pad 10 against the surface of the tongue plate 22. The top of the housing 21 is detachably capped by a cap 24, where the cap 24 is abutted against the top of the pressing block 23 for aiding the pressing block 23 being positioned inside the assembling recess 212. The bottom of the cap 24 has an upper inclined plane 241 to be fitted with the lower inclined plane 215, and the insert portion 131 of the sensing pad 10 is sandwiched between the upper inclined plane 241 and the lower inclined plane 215.

Figure 6:
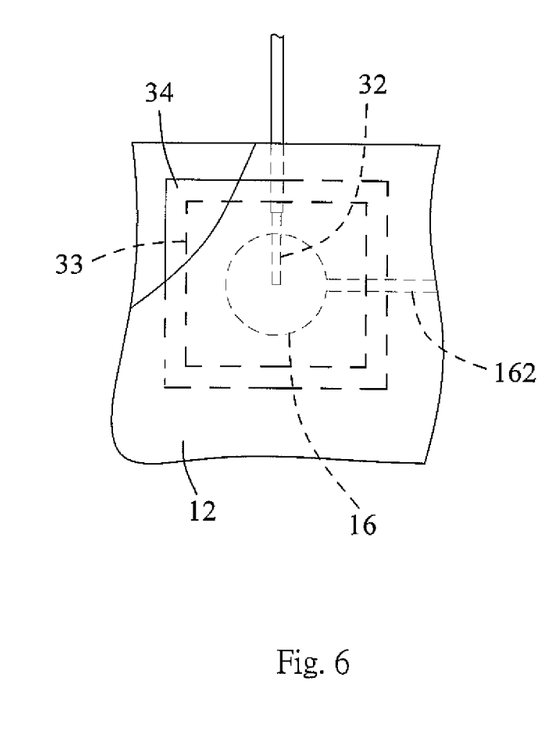
FIG. 6 is a partial plane view of where an electric wire connects to the sensing pad according to the first embodiment of the present invention.

Please refer to FIG. 2 and FIG. 6. Each of the extended electrode structures 30 has a button electrode 31, in which each of the button electrodes 31 is connected to an electric wire 32. The electric wire 32 can be conductive yarn or a metal wire. The outer end of the electric wire 32 is in between the rear sheet 11 and the front sheet 12 of the sensing pad 10, where the outer end of the electric wire 32 is contacted with and electrically connected to the connecting electrode 16. A conductive membrane 33 is adhered to the surface of the connecting electrode 16, and the outer end of the electric wire 32 is cladded by the conductive membrane 33. A fixing patch 34 is adhered to the outer side of the conductive membrane 33, in which the periphery of the fixing patch 34 is adhered to the surface of the electric film 13 for positioning the conductive membrane 33 and the outer end of the electric wire 32.

Please refer to FIG. 1 to FIG. 3. While using the present invention, taking the first preferred embodiment as an example, the front side of the front sheet 12 is adhesive, so that the sensing pad 10 can be adhered to the chest of the person to be tested. Further, seven conductive gels 15 are contacted with the skin of the chest of the person, and the button electrodes 31 of the three extended electrode structures 30 are respectively adhered to the chest of the person to be tested.

As a result, the tiny electric stimulations arising from heartbeats can be detected by the seven sensing electrodes 14 and the three button electrodes 31 of the sensing pad 10 through the human chest skin. These tiny electric stimulations are then being transferred to the first output terminal 222 and the second output terminal 223 of the connector 20 through the first terminal 141 and the second terminal 161 of the sensing pad 10. Hence, while the port 211 of the connector 20 is inserted into an ECG device, these electric signals needed for generating an ECG diagram can be then transferred to and processed via the ECG device.

One of the benefits of the present invention is that since the sensing electrode 14 of the sensing pad 10 is physically electrically connected to the first electric circuit 142, and since the electric wires 32 of each extended electrode structure 30 are adhesively electrically connected to the corresponding connecting electrodes 16, no solder process is needed. Therefore, the manufacturing costs can be effectively reduced, and the overall cost of the end-product can be lower.

Furthermore, if the first and second terminals 141/161 of the insert portion 131 are conductive ink terminals, and if the insert portion 131 is directly inserted into a receiving slot of an ECG device, debris generated during physical frictions of the insertion from the first and second terminals 141/161 might remain in the receiving slot of the ECG device, thus causing damages. Oppositely, the insert portion 131 of the present invention is connected to the receiving slot of an ECG device through the connector 20, thus no debris will be generated, and damages of the ECG device can be avoided.

Figure 7:
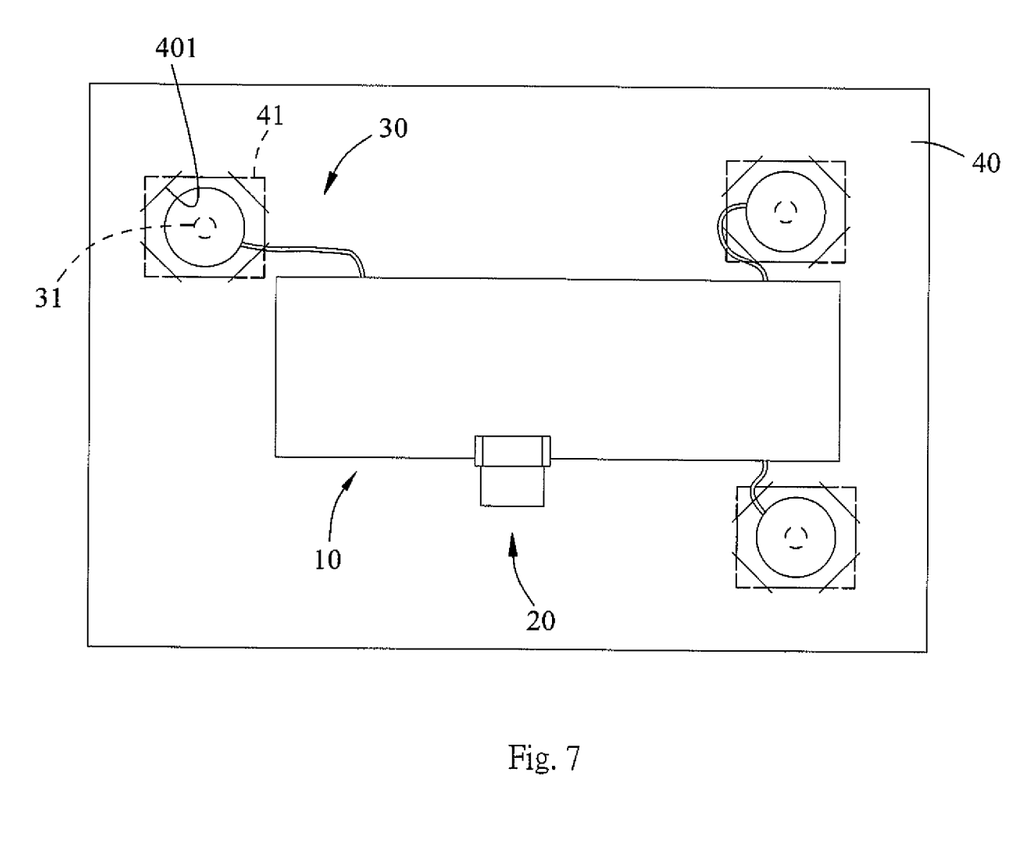
FIG. 7 is a plane view of a well-packaged electric conductive sensing device according to the first embodiment of the present invention.

Please refer to FIG. 7, while packaging the electric conductive sensing device according to the first preferred embodiment of the present invention, the device can be fixed on an adhesive film 40. The adhesive film 40 is a rectangular plastic film. The sensing pad 10 and the connector 20 are adhered to the middle of the adhesive film 40. The adhesive film 40 has three rectangular insertion plates 41 located around the peripheral portion of the adhesive film 40. Each of the extended electrode structures 30 and the button electrodes 31 are adhered to the middle of the insertion plate 41. Corresponding to the four corners of each insertion plate 41, four cutting edges 401 are formed on the adhesive film 40. The four corners of each insertion plate 41 are inserted into the corresponding cutting edges in order to be positioned. The entire electric conductive sensing device according to the first preferred embodiment of the present invention can thus be positioned and packaged on the adhesive film 40.

While the present invention is being used as ECG patches, such as the aforementioned first preferred embodiment, seven sensing electrodes 14 and three connecting electrodes 16 are located on the sensing pad 10, and the three connecting electrodes 16 are used for connecting three extended electrode structures 30. Besides, the number of the sensing electrodes 14 on the sensing pad 10 is not limited to seven, and it can be any number more than one. Likewise, the number of the connecting electrodes 16 of the sensing pad 10 and the corresponding extended electrode structures 30 can be other than three, and, more specifically, it can be any number more than one. The position of the sensing electrodes 14 and the connecting electrodes 16 on the electric film 13 can be altered according to different practical uses according to where the electric stimulations are detected.

According to the first preferred embodiment of the present invention mentioned above, the electric film 13 of the sensing pad 10 is a plastic film. The sensing electrodes 14, the first terminals 141, and the first electric circuit 142 can be formed of conductive ink and printed on the surface of the electric film 13. Other than that, the electric film 13 can also be a flexible printed circuit board by using metal membranes on the flexible printed circuit board to form terminals and electric circuits. Each of such terminals can be connected to the aforementioned button electrodes 31 through wires by soldering, as exemplified in FIGS. 8 and 9 according to the second preferred embodiment of the present invention.

The structure of the aforementioned first preferred embodiment can not only be used as ECG patches, but also be used as transcutaneous electrical nerve stimulation patches by inserting port 211 of the connector 20 into an electrical stimulator. In this instance, electric currents generated from the electrical stimulator can be transferred to the human body via the sensing electrodes 14 and the button electrodes 31, thereby enhancing blood circulation, eliminating fatigue, relieving muscle pain, or training muscles.

Figure 8:
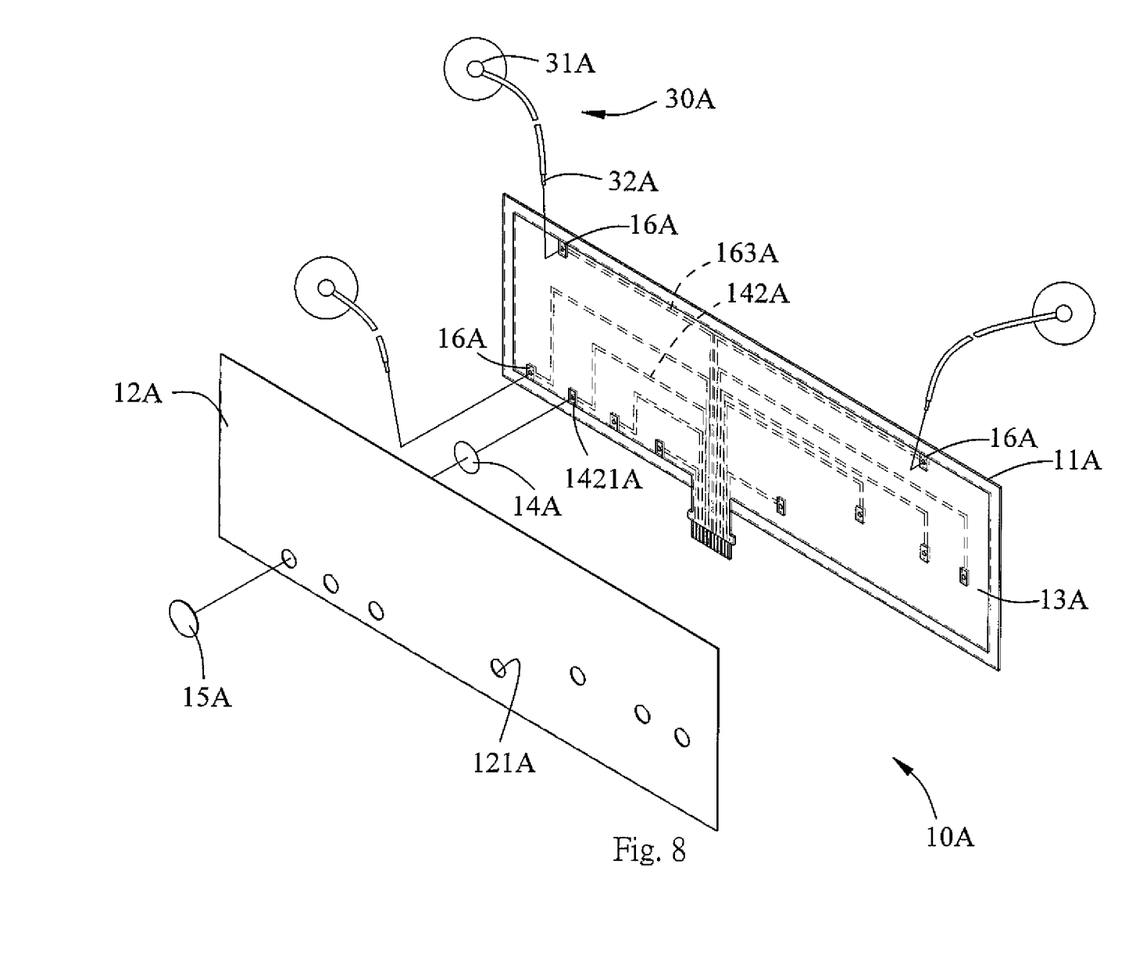
FIG. 8 is an exploded diagram illustrating a sensing pad and an extended electrode structure according to a second embodiment of the present invention.

According to the second preferred embodiment of the present invention, the sensing pad 10 has a rear sheet 11A that is adhesive, and the front side of the rear sheet 11A has a front sheet 12A. The front sheet 12A has the identical shape with the rear sheet 11A, so that the periphery of the backside of the front sheet 12A can be exactly matched with and adhered to the periphery of the front side of the rear sheet 11A. The front side of the front sheet 12A is adhesive. Seven openings 121A are located along the horizontal extension direction of the front sheet 12A. An electric film 13A is sandwiched between the front sheet 12A and the rear sheet 11A. The electric film 13A is a flexible printed circuit board. The area of the electric film 13A is smaller than the area of the rear sheet 11A or the front sheet 12A. An insert portion 131A is extended downwardly from the middle of the bottom side of the electric film 13A. The insert portion 131A is protruded out of the bottom edge of the rear sheet 11A and the front sheet 12A. Two positioning protrusions 132A are respectively protruded from the left side and the right side of the insert portion 131A.

Figure 9:
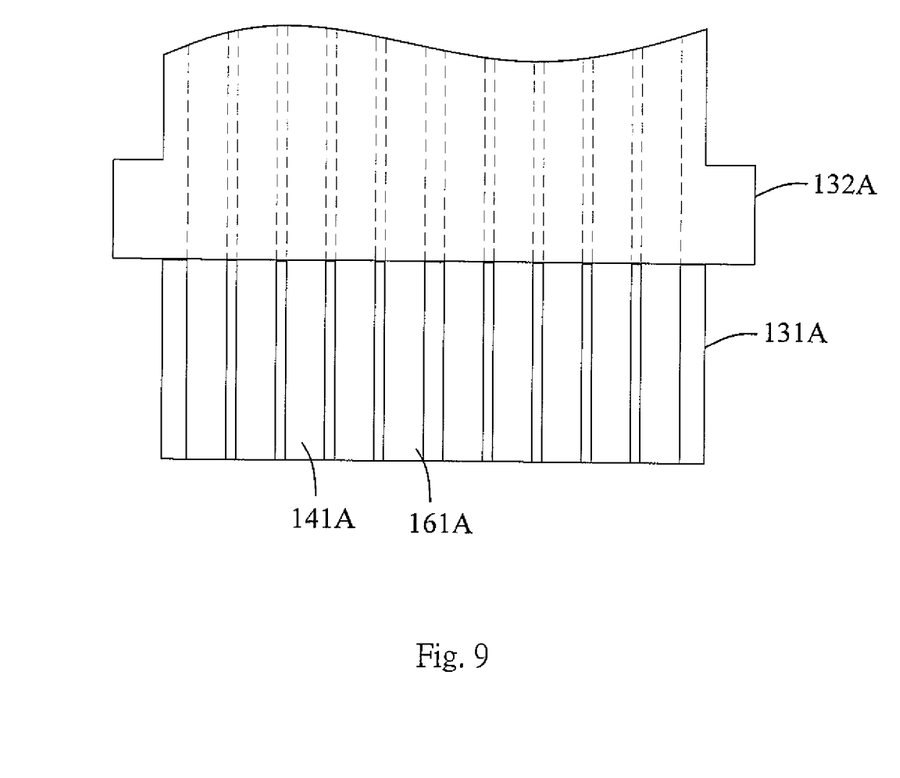
FIG. 9 is a plane view partially enlarging an insert portion according to the second embodiment of the present invention.

Corresponding to each of the seven openings 121A, a sensing electrode 14A is formed at the front side of the electric film 13A. The sensing electrodes 14A are formed of conductive ink and are printed on the surface of the electric film 13A. Each of the sensing electrodes 14A is exposed from the opening 121A. Corresponding to the number of the sensing electrodes 14A, seven first terminals 141A are formed on the insert portion 131A. The seven first terminals 141 are spaced horizontally. Each of the first terminals 141A is a metal membrane terminal formed on the surface of the insert portion 131A. Each of the first terminals 141A is connected to the corresponding sensing electrode 14A by a first electric circuit 142A. Each of the first electrical circuit 142A is a metal membrane circuit formed inside the electric film 13A. An exposing end 1421A is formed where each of the first electrical circuit 142A is connected to each of the sensing electrodes 14A. Each exposing end 1421A is covered by and electrically connected to a corresponding sensing electrode 14A. Each of the openings 121A is covered by a conductive gel 15A, where each of the conductive gels 15A is electrically connected to a corresponding sensing electrode 14A by contacting with the corresponding sensing electrode 14A.

Three connecting electrodes 16A are formed at the front side of the electric film 13A. Each of the connecting electrodes 16A is a metal membrane electrode. Corresponding to the number of the connecting electrodes 16A, three second terminals 161A, which are spaced horizontally with the seven first terminals 141A, are formed on the insert portion 131A. Each of the second terminals 161A is a metal membrane terminal formed on the surface of the insert portion 131A. Each of the second terminals 161A is connected to the corresponding connecting electrode 16A by a second electric circuit 163A. The second electric circuit 163A is a metal membrane circuit formed inside the electric film 13A.

Three extended electrode structures 30A are provided corresponding with the three connecting electrodes 16A. Each of the extended electrode structures 30A has a button electrode 31A. Each button electrode 31A is connected to an electric wire 32A. The outer end of each of the electric wires 32 is in between the rear sheet 11A and the front sheet 12A of the sensing pad 10A, where the outer end of the electric wire 32A is soldered thereby electrically connecting to the connecting electrode 16A.

The rest of the structures of the second preferred embodiment of the present invention, such as the connecting structure of the insert portion 131A of the sensing pad 10A and the connector 20, and such as the structure of positioning the sensing pad 10A and the three extended electrode structures 30A onto the adhesive film 40, and the way to practice are similar to the first embodiment and need not be repeated here.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An electric conductive sensing device comprising:
    a sensing pad having a front sheet and a rear sheet combined with the front sheet, with the front sheet having at least one opening, an electric film sandwiched between the front sheet and the rear sheet, an insert portion extended from a side of the electric film, and a sensing electrode formed on the electric film and aligned with each of the at least one opening, with each sensing electrode being a conductive ink electrode and exposed through each of the at least one opening, at least one first terminal formed on the insert portion, with each of the at least one first terminal and a corresponding sensing electrode connected together by a first electric circuit, with each of the at least one opening covered by a conductive gel, with each conductive gel electrically connected with the sensing electrode by direct contact;
    an adhesive film, wherein the sensing pad is adhered to a middle of the adhesive film;
    a connector having the insert portion of the sensing pad integrated in a tongue plate installed in the connector, and at least one first output terminal disposed on the tongue plate, with each of the at least one first output terminal electrically connected with each of the at least one first terminal, wherein the connector is adhered to the middle of the adhesive film with the sensing pad;
    at least one connecting electrode formed on the electric film;
    a button electrode connected with an electric wire disposed corresponding to each at least one connecting electrode, wherein an outer end of the electric wire is in between the rear sheet and the front sheet of the sensing pad, wherein the outer end of the electric wire is soldered on to the at least one connecting electrode; and
    a rectangular insertion plate disposed corresponding to each button electrode, wherein each button electrode is adhered to a middle of the rectangular insertion plate, wherein the adhesive film has four cutting edges corresponding to four corners of the rectangular insertion plate, and wherein the four corners of the rectangular insertion plate are respectively inserted into the four cutting edges.

2. The electric conductive sensing device according to claim 1, wherein the electric film is a plastic film, wherein each of the at least one first terminal is formed of conductive ink and is printed on a surface of the insert portion, and wherein each first electric circuit is formed of a conductive ink and is printed on a surface of the electric film.

3. The electric conductive sensing device according to claim 2, wherein the insert portion is extended downwardly from a bottom side of the electric film, wherein two positioning protrusions are respectively protruded from a left side and a right side of the insert portion; wherein the connector has a housing, wherein a bottom of the housing has a port, wherein a top of the housing has an assembling recess, wherein a tongue slot is penetrated throughout the assembling recess and the port, wherein two positioning grooves are respectively located at both sides of the tongue slot, wherein a lower inclined plane is interiorly formed at a front side of the assembling recess, and wherein an edge of the top of a front side of the housing has a notch connected with the lower inclined plane;

wherein the tongue plate is penetrated through the tongue slot, wherein the tongue plate has two positioning flanges respectively protruded from a left side and a right side of the tongue plate, wherein the two positioning flanges are respectively received by the two positioning grooves; wherein the insert portion is inserted into the notch, along the lower inclined plane, and finally lapping the tongue plate, wherein the two positioning protrusions of the insert portion are respectively received by the two positioning grooves; wherein a pressing block is located in the assembling recess, the pressing block has a pressing portion, wherein the pressing portion presses the insert portion in order to tightly press the insert portion against a surface of the tongue plate, wherein the top of the housing is detachably capped by a cap, wherein the cap is abutted against a top of the pressing block, wherein a bottom of the cap has an upper inclined plane to be fitted with the lower inclined plane, and wherein the insert portion is sandwiched between the upper inclined plane and the lower inclined plane.

4. The electric conductive sensing device according to claim 2, wherein the at least one connecting electrode is an electrode formed of printed conductive ink, wherein at least one second terminal is formed on the insert portion, wherein the at least one second terminal is printed on a surface of the insert portion and is formed of conductive ink, wherein the at least one second terminal and a corresponding connecting electrode is connected by a second electric circuit, wherein the second electric circuit is printed on a surface of the electric film and is formed of conductive ink, wherein the tongue plate has at least one second output terminal formed thereon and connected with the at least one second terminal;

wherein a conductive membrane is adhered to a surface of the at least one connecting electrode, wherein the outer end of the electric wire is cladded by the conductive membrane, wherein a fixing patch is adhered to an outer side of the conductive membrane, and wherein a periphery of the fixing patch is adhered to the electric film for positioning the conductive membrane and the outer end of the electric wire.

5. The electric conductive sensing device according to claim 1, wherein the electric film is a flexible printed circuit board, wherein each of the at least one first terminal is a metal membrane terminal formed on a surface of the insert portion, wherein each first electric circuit is a metal membrane circuit formed inside the electric film, wherein an exposing end is formed where each first electric circuit is connected to each sensing electrode, and wherein each sensing electrode is electrically connected to each exposing end by covering each exposing end.

6. The electric conductive sensing device according to claim 5, wherein the insert portion is extended downwardly from a bottom side of the electric film, wherein two positioning protrusions are respectively protruded from a left side and a right side of the insert portion; wherein the connector has a housing, wherein a bottom of the housing has a port, wherein a top of the housing has an assembling recess, wherein a tongue slot is penetrated throughout the assembling recess and the port, wherein two positioning grooves are respectively located at both sides of the tongue slot, wherein a lower inclined plane is interiorly formed at a front side of the assembling recess, and wherein an edge of the top of a front side of the housing has a notch connected with the lower inclined plane;

wherein the tongue plate is penetrated through the tongue slot, wherein the tongue plate has two positioning flanges respectively protruded from a left side and a right side of the tongue plate, wherein the two positioning flanges are respectively received by the two positioning grooves; wherein the insert portion is inserted into the notch, along the lower inclined plane, and finally lapping the tongue plate, wherein the two positioning protrusions of the insert portion are respectively received by the two positioning grooves; wherein a pressing block is located in the assembling recess, the pressing block has a pressing portion, wherein the pressing portion presses the insert portion in order to tightly press the insert portion against a surface of the tongue plate, wherein the top of the housing is detachably capped by a cap, wherein the cap is abutted against a top of the pressing block, wherein a bottom of the cap has an upper inclined plane to be fitted with the lower inclined plane, and wherein the insert portion is sandwiched between the upper inclined plane and the lower inclined plane.

7. The electric conductive sensing device according to claim 5, wherein the at least one connecting electrode is a metal membrane electrode, wherein at least one second terminal is formed on the insert portion, wherein the at least one second terminal is a metal membrane terminal formed on the insert portion, wherein the at least one second terminal and a corresponding connecting electrode is connected by a second electrical circuit, wherein the second electric circuit is a metal membrane circuit formed in an interior of the electric film, and wherein the tongue plate has at least one second output terminal formed thereon and connected with the at least one second terminal.

8. The electric conductive sensing device according to claim 1, wherein the insert portion is extended downwardly from a bottom side of the electric film, wherein two positioning protrusions are respectively protruded from a left side and a right side of the insert portion; wherein the connector has a housing, wherein a bottom of the housing has a port, wherein a top of the housing has an assembling recess, wherein a tongue slot is penetrated throughout the assembling recess and the port, wherein two positioning grooves are respectively located at both sides of the tongue slot, wherein a lower inclined plane is interiorly formed at a front side of the assembling recess, and wherein an edge of the top of a front side of the housing has a notch connected with the lower inclined plane;

wherein the tongue plate is penetrated through the tongue slot, wherein the tongue plate has two positioning flanges respectively protruded from a left side and a right side of the tongue plate, wherein the two positioning flanges are respectively received by the two positioning grooves; wherein the insert portion is inserted into the notch, along the lower inclined plane, and finally lapping the tongue plate, wherein the two positioning protrusions of the insert portion are respectively received by the two positioning grooves; wherein a pressing block is located in the assembling recess, the pressing block has a pressing portion, wherein the pressing portion presses the insert portion in order to tightly press the insert portion against a surface of the tongue plate, wherein the top of the housing is detachably capped by a cap, wherein the cap is abutted against a top of the pressing block, wherein a bottom of the cap has an upper inclined plane to be fitted with the lower inclined plane, and wherein the insert portion is sandwiched between the upper inclined plane and the lower inclined plane.

\* \* \* \* \*